(12) United States Patent
Garbellotto et al.

(10) Patent No.: US 10,012,635 B2
(45) Date of Patent: Jul. 3, 2018

(54) SYSTEM, MACHINE AND METHOD FOR CHARACTERIZING WOODEN PART-COMPONENTS IN ORDER TO MAKE FOOD-GRADE WOODEN CONTAINERS

(71) Applicant: GIOBATTA E PIERO GARBELLOTTO S.p.A., Conegliano (IT)

(72) Inventors: Piero Garbellotto, Conegliano (IT); Franco Battistutta, Conegliano (IT)

(73) Assignee: Giobatta E Piero Garbellotto S.p.A., Conegliano (IT)

( * ) Notice: Subject to any disclaimer, the term of this patent is extended or adjusted under 35 U.S.C. 154(b) by 269 days.

(21) Appl. No.: 14/504,281

(22) Filed: Oct. 1, 2014

(65) Prior Publication Data
US 2015/0097121 A1   Apr. 9, 2015

(30) Foreign Application Priority Data
Oct. 3, 2013 (EP) ..................... 13187284

(51) Int. Cl.
| | | |
|---|---|---|
| G01J 5/02 | (2006.01) | |
| G01N 21/35 | (2014.01) | |
| G01N 33/46 | (2006.01) | |
| G01N 21/3563 | (2014.01) | |
| G01N 21/359 | (2014.01) | |

(52) U.S. Cl.
CPC ........... *G01N 33/46* (2013.01); *G01N 21/359* (2013.01); *G01N 21/3563* (2013.01); *G01N 2201/02* (2013.01)

(58) Field of Classification Search
CPC ........... G01N 33/46; G01N 2021/8466; G01N 33/146; G01N 21/3563
USPC ........................................ 250/341.1, 341.8
See application file for complete search history.

(56) References Cited

U.S. PATENT DOCUMENTS

2013/0222799 A1*  8/2013  Ashok ............... B01L 3/502715
356/301

FOREIGN PATENT DOCUMENTS

FR    2 971 967 A1    8/2012

OTHER PUBLICATIONS

Haalan et al. "Partial Least-Squares Methods for Spectral Analyses. 1. Relation to Other Quantitative Calibration Methods and the Extraction of Qualitative Information," Analytical Chemistry 1988 60 (11), pp. 1193-1202.*

(Continued)

Primary Examiner — David Porta
Assistant Examiner — Carolyn Igyarto
(74) Attorney, Agent, or Firm — Klarquist Sparkman, LLP

(57) ABSTRACT

A method for characterizing food-grade wooden part-components, characterized in that it comprises the steps of: emitting an IR radiation beam towards food-grade wooden part-components, receiving radiations reflected/transmitted by the radiated wooden part-components, processing said radiations reflected/transmitted by the radiated food-grade wooden part-components to generate information indicative of the radiation spectrum, determining, on the basis of said spectrum, the quantities PE(i) of odor active volatile compounds present in the food-grade wooden part-components, and characterizing said wooden part-components on the basis of determined quantities PE(i) of odor active volatile compounds.

14 Claims, 2 Drawing Sheets

(56) References Cited

OTHER PUBLICATIONS

European Search Report for European Patent Application No. EP 13 18 7284, dated Feb. 25, 2014, 7 pages.

Michel et al., "Impact of Concentration of Ellagitannins in Oak Wood on Their Levels and Organoleptic Influence in Red Wine," *Journal of Agricultural and Food Chemistry*, vol. 59, No. 10, May 25, 2011, pp. 5677-5680.

Giordanengo et al., "Oakscan: procédé de mesure rapide et non destructif des polyphénols du bois de chêne de tonnellerie," retrieved from the Internet: URL:http://hal.cirad.fr/docs/00/65/42/22/PDF/MO2009-PUB00032880.pdf.[retrieved on Feb. 25, 2014], Dec. 21, 2011, pp. 1-12.

Taylor et al., "NIR-based prediction of extractives in American white oak heartwood," *Holzforschung*, vol. 65, pp. 185-190, 2011.

Cadet et al., "Review: Quantitative Analysis, Infrared," *Encyclopedia of Analytical Chemistry, Online*, Oct. 2012 [https://www.researchgate.net/profile/Frederic_Cadet/publication/258837146_Review_Quantitative_Analysis_Infrared_october_2012/links/00463529215342c984000000/Review-Quantitative-Analysis-Infrared-october-2012.pdf?origin=publication_detail] retrieved on Aug. 17, 2017.

Labbe, "Extracting information from spectral data," *SWST, Advanced analytical tools for the wood industry*, The University of Tennessee, Jun. 10, 2007 [http://www.swst.org/meetings/AM07/labbe.pdf] retrieved on Aug. 17, 2017.

Doussot et al. "Individual, species and geographic origin influence on cooperage oak extractible content (*Quercus robur* L. and *Quercus petraea* Liebl.)" *Analusis*, vol. 28, No. 10, pp. 960-965 (Dec. 2000).

Prida et al. "Influence of Geographical Origin and Botanical Species on the Content of Extractives in American, French, and East European Oak Woods." *Journal of Agricultural and Food Chemistry*, vol. 54, No. 21, pp. 8115-8126 (Oct. 1, 2006).

\* cited by examiner

SYSTEM, MACHINE AND METHOD FOR CHARACTERIZING WOODEN PART-COMPONENTS IN ORDER TO MAKE FOOD-GRADE WOODEN CONTAINERS

CROSS REFERENCE TO RELATED APPLICATION

This application claims priority from European Patent Application No. 13187284.8, filed on Oct. 3, 2013 and published as EP2857826A1, which is hereby incorporated by reference.

FIELD

The present invention relates to the processing of food-grade wood, preferably although not necessarily for wine-making, and in particular relates to a system configured to divide/separate, in completely automatic manner, the wooden part-components into predetermined categories of food-grade wood, such as, for example, wood chips and/or planks/staves designed to be used to make a container for containing/refining wine or a wine-related product or a distillate, to which reference will be made in the following description without thereby losing in generality.

BACKGROUND

It has been known for centuries that a wine containing barrel made with wooden staves considerably influences the aroma (bouquet), the perfume, and the color of the wine itself during the wine preservation/aging process, and may thus have different/variable effects on the wine according to the type of wood and its composition. In detail, a wooden barrel is used to contain great aromatic red wine, such as Brunello, Chateaux etc., but it may be also used for valuable vinegar and distillates because its aromatic contribution is essential for achieving the latter.

Currently, the wood for making staves usable for making a barrel is chosen by means of empiric methods, which are essentially based on analyzing the correlation between the wood composition and some data, such as: the geographic origin of the wood, the growth factors of the trees and the environmental factors. Such methods thus require carrying out long, complex analyses at the origin of the woods with all the drawbacks that this implies in terms of costs and productive efficiency. Furthermore, the evaluation and final choice of the wood, i.e. the categorization of the wood for making a barrel, is carried out by an operator, who analyzes the aforesaid data/correlations and establishes the type of wood to be used on the basis of experience. It is apparent that such a procedure is subject to considerable margins of error because the final choice of the wood for making the barrel is entirely subjective.

The applicant has carried out an in-depth study to provide a system for categorizing food-grade wooden part-components preferably, although not necessarily, for wine-making, i.e. oenological use, which: allows to divide, i.e. to catego-rize, the wooden part-components on the basis of an objective analysis depending on quantities of odor active volatile compounds present in the wood designed, in use, to specifically condition the aroma/perfume of a wine or any wine-derived product such as for example vinegar, or a distillate product, which rapidly provides the information concerning the category to which the analyzed wood belongs, is simple to use by an operator, and is easy to implement on an industrial production line/system of staves for barrels/vats.

SUMMARY

It is thus the object of the present invention to make available a solution which allows to reach the objectives indicated above.

This object is reached by the present invention in that it relates to a system, a method and a machine for categorizing food-grade wooden part-components, preferably for winemaking, as disclosed in the appended claims.

BRIEF DESCRIPTION OF THE DRAWINGS

The present invention will now be described with reference to the accompanying drawings, which show a non-limitative embodiment thereof, in which:

FIG. 1 diagrammatically shows a system for categorizing food-grade wooden part-components according to the dictates of the present invention; while

DETAILED DESCRIPTION

The present invention will now be described in detail with reference to the accompanying drawings in order to allow a person skilled in the art to implement and use it. Various changes to the described embodiments will be immediately apparent to a person skilled in the art, and the described generic principles may be applied to other embodiments and applications without thereby departing from the scope of protection of the present invention, as disclosed in the appended claims. Therefore, the present invention must not be considered limited to the described and illustrated embodiments, but instead confers the broadest scope of protection, in accordance with the principles and features described and disclosed herein.

Figure 1:
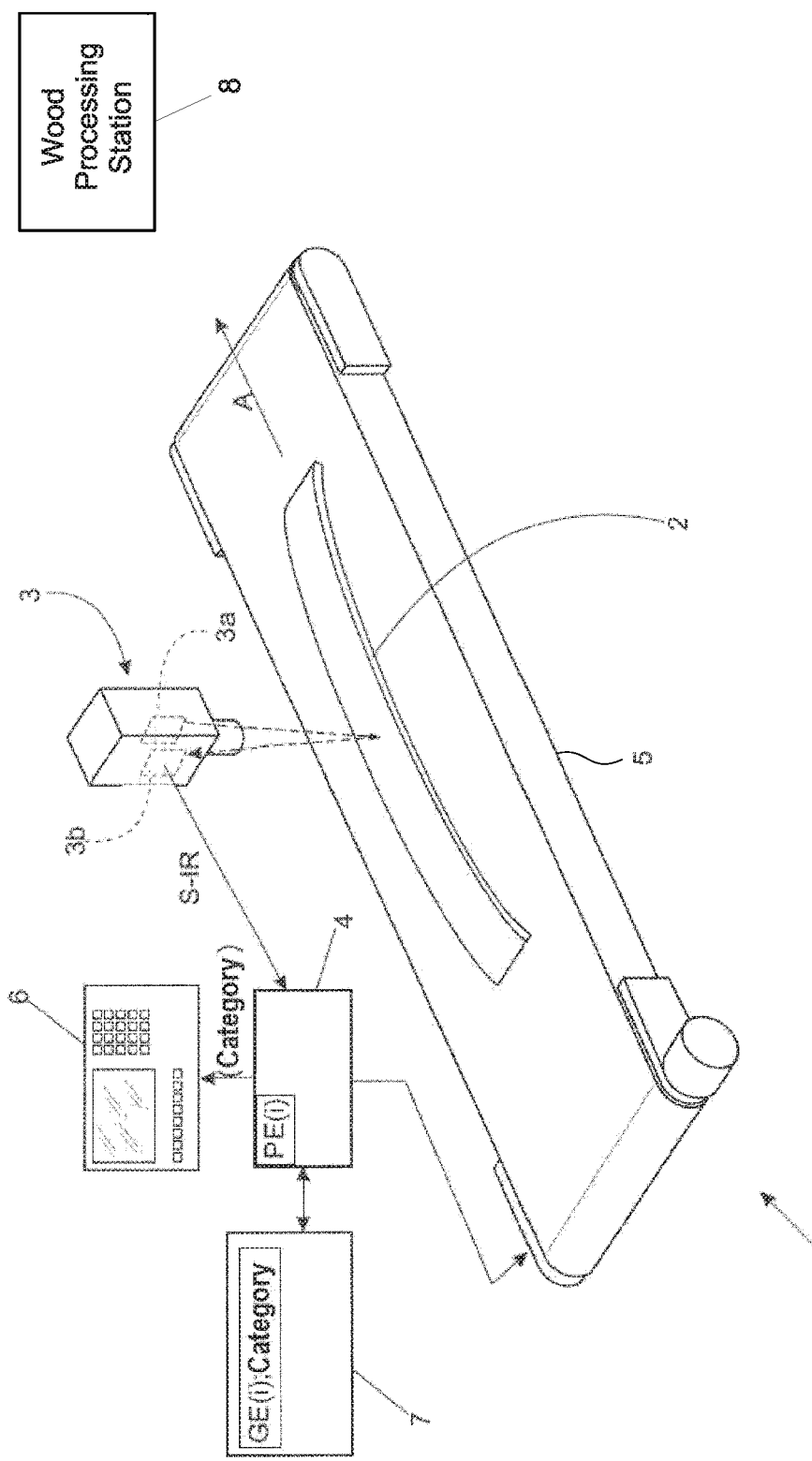

With reference to FIG. 1, numeral 1 indicates, as a whole, a system for categorizing food-grade wooden part-components 2, preferably although not necessarily for wine-making, i.e. oenological use, which is configured so as to analyze the wooden part-components to determine quantities PE(i), (i) being variable between 1 and n, of odor active volatile compounds present in the wood. It is pointed out that with the term "quantity of odor active volatile compounds" it is understood any value which is indicative of the quantity, such as, for example, the percentage of odor active volatile compounds. In this connection, it is pointed out that in the present invention the term odor active volatile compounds is understood under the sensorial point of view usually used in the oenological field.

Differently from the tannin which specifically conditions the "wine structure" (which may be soft or hard depending on the quantity of tannin), the quantity of odor active volatile compounds, contained in the wood used for a barrel, specifically conditions the perfume/aroma of the wine.

According to a preferred embodiment, the wooden part-components 2 may comprise rough planks or semi-machined planks or machined wooden planks, e.g. wooden staves, preferably but not necessarily made of oak heartwood, which may be assembled in known manner to obtain a container or vessel designed to contain or refine wine or a wine-derived product.

It is pointed out that with the term wine-derived product it is understood a vinegar or a wine distillate like, for example, cognac, brandy, grappa or similar.

Moreover, it is pointed out that with container it is understood any opened or closed container such as, for example, small barrels (in Italian language, botticelle), barrels, casks, barriques, or vats, designed to contain wine during its ageing for refining the wine.

It is moreover understood that although the present description refers to wooden part-components 2 to use for oenology, the present invention is not limited to this specific use, but it may also be used to characterize wood to make barrels designed to contain other kinds of alcoholic beverages generally aged/refined in wooden barrels. These alcoholic beverages may contain: beer, distillates of cereal (grain, corn, barley, rye) such as, for example, whisky, or sugar cane distillates such as rum, and other alcoholic distillates having different origin but aged in wooden barrels.

It is understood that in all cases, the present invention is not limited to this type of application, but may be used additionally or alternatively to characterize wooden part-components 2 corresponding to wood chips (not shown) designed either to be immersed in or to be put into contact with a wine according to refinement methods of the known type and thus not described in detail.

According to a preferred embodiment, the system 1 is configured so as to execute a spectrographic analysis on the wooden part-components 2 so as to determine a value indicative of quantity PE(i) of one or more odor active volatile compounds on the basis of the detected spectrum and to categorize the wooden part-components 2 (i.e. to determine the belonging of the examined wooden part-components 2 to a predetermined category of food-grade wood, preferably for oenology use) on the basis of said determined quantity PE(i) of odor active volatile compounds.

Preferably, the system 1 may be configured so as to compare quantities PE(i) of one or more aromatic compounds with corresponding predetermined magnitudes/quantities GE(i) associated with corresponding pre-established thresholds of odor active volatile compounds and to categorize the wooden part-component 2 on the basis of the result of said comparison.

According to a preferred embodiment shown in FIG. 1, the system 1 is configured to execute a spectroscopic analysis to determine the quantities PE(i) of odor active volatile compounds present in the wood by preferably operating in the near-infrared wavelength band, i.e. in the NIR (Near-IR) band, which is known and comprised between approximately 780 nm and 2500 nm.

According to a possible embodiment, the system 1 may be configured so as to execute a spectroscopic analysis to determine the quantity PE(i) of odor active volatile compounds by preferably operating in the mid-infrared wavelength band, i.e. the MIR (MID-IR) band, which is known and comprised between approximately 2500 nm and 50000 nm.

According to a preferred embodiment shown in FIG. 1, the system may comprise an IR spectroscopic apparatus 3, which is structured so as to be arranged, in use, at/near a wooden part-component 2 to be categorized and is configured so as to: emit an IR radiation beam (infrared radiation) towards said wooden part-component 2; receive some of the radiations obtained by reflection/transmission of the incident IR radiation beam from the wooden part-component 2 and provide an S-IR analysis signal containing information indicative of the received electromagnetic radiation spectrum. It is understood that in all cases the present invention is not limited to analyzing the reflection of electromagnetic radiations by the wooden part-component 2, but may also additionally or alternatively relate to the transmission of the electromagnetic radiations obtained following the crossing of the wooden part-component 2 by the incident IR electromagnetic radiations.

According to a preferred embodiment, the system 1 further comprises an electronic processing device 4, which may be connected to the IR spectroscopic apparatus 3 to receive the S-IR analysis signal, and is configured so as to process the S-IR analysis signal, by means of a spectrum analysis/processing algorithm, so as to determine one or more quantities PE(i) of one or more of odor active volatile compounds on the basis of the spectrum and to categorize the wooden part-component 2 on the basis of the determined quantities PE(i).

It is pointed out that the kind of odor active volatile compounds used by the system 1 to categorize the wood depends on the use of the food-grade wooden part-component 2. In detail, odor active volatile compounds used by the system 1 to categorize the wood for barrels containing wine may be different from odor active volatile compounds used to categorize the wood for barrels containing vinegar, wine distillates, beer, or cereals distillate.

The odor active volatile compounds determined by the electronic processing device 4 may comprise lactones, eugenol, vanillin, volatile phenols, aldehydes or the like.

It is pointed out that tannin is not an odor active volatile compound.

The quantities PE(i) of odor active volatile compounds may be determined by the analysis/processing algorithms by using predetermined correlation functions on the basis of the measured spectrum. The correlation functions associated with the quantities PE(i) of odor active volatile compounds may be determined/established by means of multivariate PCA (Principal Component Analysis) or PLS (Partial Least Squares) statistic processing methods/tests of known type applied to a series of samples data associated with the quantities PE(i) of odor active volatile compounds presents in pre-established wood, and to the corresponding bands/wavelengths.

In this connection, Applicant has found that odor active volatile compounds are in the wood in very small percentage/quantities, the order of some milligrams per kilogram of wood. As a consequence, odor active volatile compounds cannot be measured through a direct NIR measure which, on the contrary, may be used to measure other kind of compounds present in the wood in high quantities, such as, for example, the tannin (order of ten grams per kilogram of wood) or the water (order of about a hundred grams per kilogram of wood). In this respect, Applicant has found that odor active volatile compounds can be measured in indirect manner, by performing analysis/processing algorithms using predetermined correlation functions disclosed above.

According to a preferred embodiment, the system 1 may establish one or more categories of food-grade wood, preferably wood for wine-making, which may be characterized, for example, by one or more predetermined reference magnitudes/quantities GE(i) associated with respective quantities PE(i) of odor active volatile compounds. The electronic processing device 4 may be configured so as to establish/determine whether a wooden part-component 2 belongs to a determined category of food-grade wood, preferably for wine-making, when one or more quantities PE(i) of odor active volatile compounds satisfy at least one predetermined relationship/condition with the respective predetermined magnitudes/quantities GE(i).

According to a possible embodiment, the electronic processing device 4 may be configured so as to establish/determine whether the wooden part-component 2 belongs to a category of food-grade wood when one or more quantities PE(i) of odor active volatile compounds are higher than the respective predetermined magnitude/quantity GE(i).

By way of non-limiting example only, electronic processing device 4 may establish the belonging of part of a wooden part-component 2 to said category of wood, e.g. a first category, when the quantities PE(i) of odor active volatile compounds, for example the vanillin is higher than a respective quantity GE(i) which is indicative of a vanillin threshold associated with the first category.

According to a possible embodiment, the electronic processing device 4 may be configured so as to establish/determine that the wooden part-component 2 belongs to a determined category of food-grade wood, preferably for wine-making, e.g. to a second category, when one or more quantities PE(i) of odor active volatile compounds are comprised in a predetermined range associated to with the respective predetermined quantity/magnitude GE(i). According to a non-limiting example, the predetermined magnitudes GE(i) characterizing each category of wood may comprise a predetermined odor active volatile compounds range ΔA. In this case the electronic processing device 4 may determine the belonging of part of a wooden part-component 2 to said category of wood, e.g. a second category, when the quantity of the odor active volatile compound is comprised within the predetermined odor active volatile compounds range ΔA.

It is understood that in all cases, the present invention is not limited to the exceeding of the aforesaid predetermined ratios of thresholds and to the inclusion of the quantities PE(i) within predetermined range ΔA, but according to the possible variants, other ratios between the quantities PE(i) and the predetermined magnitudes/quantities GE(i) associated with the predetermined categories may be included, in which each ratio, e.g. determined by a mathematical equation, may depend on the categorization of the wood and of the type of wood, or on the quantities of odor active volatile compounds PE(i)/magnitudes GE(i) used for the comparison.

The spectroscopic apparatus IR 3 is a known device and thus will not be further described unless to specify that that it may comprise an IR emitting device controlled 3a to emit the IR radiation beam having a wavelength in the infrared band towards the wooden part-component 2 corresponding, for example, to a stave, and an infrared sensitive detection device 3b, which is configured to receive the radiation beam from the stave 2 (in the example illustrated in FIG. 1) and to provide the S-IR analysis signal containing the spectrum.

According to a possible embodiment shown in FIG. 1, the system 1 may preferably, but not necessarily comprise an actuating device 5, which is structured to move/advance the wooden part-components 2, preferably one after the other, along a direction of advancement A, so that the IR radiation beam hits the wooden part-components 2. For this purpose, the actuating device 5 may comprise a motorized conveyor belt or any other known advancement device type designed to move the wooden part-components 2, e.g. the staves, under the bias of the processing device 4, so as to have them irradiated by the IR radiation beam.

According to a possible embodiment shown in FIG. 1, the IR spectroscopic apparatus 3 is arranged above the actuating device 5 so as to radiate the wooden part-component 2 positioned on the advancement plane of the actuating device 5. Preferably, the analysis may be carried out on the greater surface of the stave 2, commonly indicated as "back", to determine some conditioning parameters PE(i), and/or on a smaller side surface of the stave 2, commonly known as "side" to determine the other conditioning parameters PE(i).

The IR spectroscopic apparatus 3 may be fixed or supported by an appropriate frame (not shown), or may be displaced manually in space, or may be structured to be grasped by the operator and manually positioned in a position facing the wooden part-component 2 to be characterized/categorized.

According to a possible embodiment shown in FIG. 1, the system 1 may preferably comprise a user interface 6, which is connected to the electronic processing device 4 and is structured so as to allow an operator to input commands to the system 1, e.g. an advancement control of the staves and/or a control to establish/set the category of the food-grade wood and/or a command to establish the magnitudes GE(i) and/or the ratios associated with one or more categories of wood and/or to receive the information from the system itself, preferably the indication relative to the category to which the analyzed wooden part-component 2 belongs. According to a possible embodiment shown in FIG. 1, the user interface 6 may comprise a display and/or a control keyboard and/or a similar interface device/apparatus of visual and/or auditory and/or vocal type.

According to a possible embodiment, the system 1 may preferably comprise a storage device 7 containing the predetermined wood categories and, preferably but not necessarily, the respective predetermined magnitudes GE(i) for each wood category. For example, the storage device 7 may comprise an electronic table or database preferably containing, for each wood category, the respective values of the predetermined quantities/magnitudes GE(i) and the corresponding predetermined ratios to be satisfied for categorizing the wood.

Furthermore, the spectrum algorithms for determining the quantities PE(i) and the correlation functions which may be implemented in use by the electronic control device 4 for determining the quantities PE(i) of odor active volatile compounds on the basis of the information indicating the spectrum contained in the S-IR analysis signal can be stored in the form of programs in the storage device 7.

Figure 2:
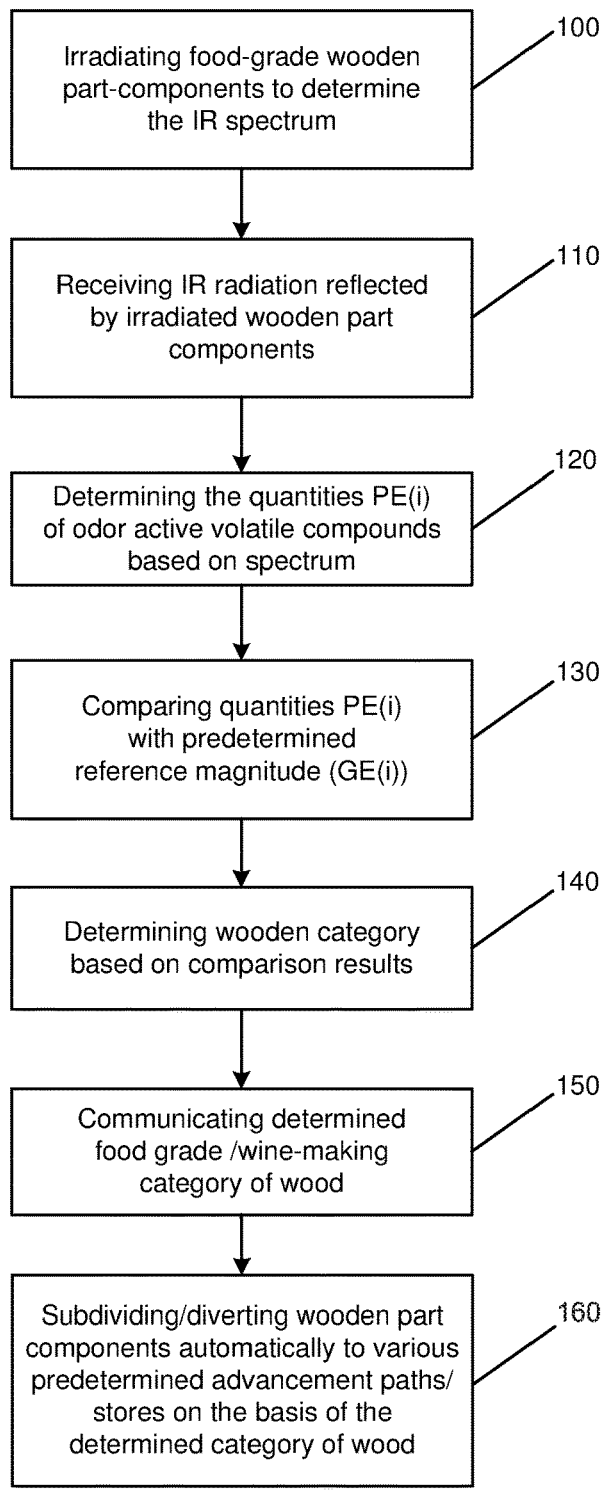
FIG. 2 is a flow chart of the operative steps of the method for categorizing the food-grade wooden part-components, provided according to the present invention.

FIG. 2 shows a flow chart indicating the operations implemented by the method for characterizing the wooden part-components in which it is supposed to execute the operations by means of the system 1 shown in FIG. 1. The method may preferably comprise arranging the stave 2, for example, on the support/advancement plane of the actuating device 5. The method performs the steps of: generating an IR radiation beam towards the wooden part-component 2 (block 100), e.g. towards the stave 2; receiving the radiations reflected/transmitted by the wooden part-component 2 (block 110), e.g. the stave 2; generating the S-IR analysis signal containing the spectrum on the basis of the detected reflected/transmitted radiations, preferably by means of the IR spectroscopic apparatus 3. Furthermore, the method performs the steps of determining one or more quantities PE(i) of odor active volatile compounds on the basis of the information contained in the S-IR analysis block indicative of the detected spectrum (block 120). For this purpose, the method may execute the required operations in analysis algorithms based on the correlation functions so as to determine, for example, the content percentage of lactones, eugenol, vanillin, volatile phenols, and/or aldehydes on the basis of the spectrum.

The method further executes the steps of categorizing the wooden part-component 2, e.g. the stave, on the basis of the quantities PE(i) of odor active volatile compounds PE(i) determined during the previous step. For this purpose, the method may execute the step of determining the category of wood, preferably for wine-making, to which the wooden part-component 2, e.g. the stave, belongs on the basis of the quantities PE(i) of odor active volatile compounds. Preferably, the method may execute the step of determining the category of wood, preferably for wine-making (e.g. the first or the second or the third category) to which the wooden part-component 2, e.g. the stave, belongs on the basis of the result of the quantities PE(i) of odor active volatile compounds and the predetermined magnitudes GE(i) associated with one or more predetermined categories of food-grade wood (block 130). Preferably, the method may execute the step of determining the wooden part-component 2, e.g. the stave, belonging to a category of wood, when one or more of the quantities PE(i) of odor active volatile compounds meet/satisfy at least one predetermined condition with the respective predetermined magnitudes GE(i) (block 140).

Preferably, the method may establish/determine the belonging of the wooden part-component 2 to a predetermined category of wood, when one or more quantities PE(i) of odor active volatile compounds are, for example, higher than the respective predetermined magnitude GE(i). These operations may be executed by the method by means of the electronic processing device 4 shown in FIG. 1. Preferably, the method may perform the step of communicating the determined category of wood to the operator (block 150). This operation may be executed preferably by means of the user interface 6. In all cases, it is understood that the present invention is not limited to communicating the determined category of wood to the operator, but may include communicating the information related to the determined category of wood to a wood processing station 8 arranged downstream of the IR spectrometric apparatus and structured to receive the wooden part-components 2, e.g. the staves, and to subdivide/divert them automatically to the various predetermined advancement paths/stores on the basis of the determined category of wood (block 160).

The system described above is advantageous because: it allows to categorize the wooden part-components on the basis of an objective analysis carried out on the compounds present in the wood, it is simple, cost-effective and rapid to execute, and it is easy to implement on an industrial production line/system of vats/barrels made using wooden staves.

It is finally apparent that changes and variations may be made to the system, machine and method described and illustrated without thereby departing from the scope of the invention defined by the accompanying claims.

In particular, the system 1 described above may correspond to a machine structured to categorize the wooden part-components for wine-making operating according to the method described above.

We claim:

1. A method for categorizing food-grade wooden part-components and making wine barrels, comprising the steps of:
    irradiating the food-grade wooden part-components with IR radiation;
    receiving IR radiation reflected and/or transmitted by the irradiated food-grade wooden part-components;
    generating a signal (S-IR) representing the radiation spectrum of the received IR radiation;
    determining on the basis of said signal, the quantities (PE(i)) of odor active volatile compounds comprising lactones and/or eugenol present in the food-grade wooden part-components which, in use, condition the aroma/perfume of a wine, or wine-related product when the wine, or wine-related product, is put into contact with the food-grade wooden part-components themselves;
    comparing at least said determined quantities (PE(i)) of odor active volatile compounds comprising lactones and/or eugenol with at least one predetermined reference magnitude (GE(i)) associated with a predetermined category of food-grade wood;
    categorizing said food-grade wooden part-components on the basis of the determined quantities (PE(i)) of odor active volatile compounds comprising lactones and/or eugenol;
    wherein categorizing comprises determining whether the food-grade wooden part-components belong to said predetermined category of food-grade wood on the basis of said comparison;
    sorting each of the food-grade wooden part-components to one of at least two paths or stores on the basis of the categorizing;
    and assembling said categorized wooden part-components into said wine barrels.

2. The method according to claim 1, further comprising:
    establishing at least a predetermined correlation function associated with quantities (PE(i)) of odor active volatile compounds to be determined; and
    performing an analysis algorithm to elaborate said spectrum of radiations reflected and/or transmitted by the irradiated food-grade wooden part-components by means of said predetermined correlation function in order to determine the quantities (PE(i)) of odor active volatile compounds.

3. The method according to claim 2, wherein:
    said predetermined correlation function is established by means of multivariate PCA (Principal Component Analysis) or PLS (Partial Least Squares) statistic processing methods/tests applied to a series of samples data associated with the quantities (PE(i)) of odor active volatile compounds comprising lactones and/or eugenol, present in pre-established wood, and to the corresponding bands/wavelengths.

4. The method according to claim 1, wherein said food-grade wooden part-components comprise wine, or a wine-related product.

5. The method according to claim 1, wherein said food-grade wooden part-components comprise wine refinement chips.

6. The method according to claim 1, wherein said food-grade wooden part-components comprise at least one plank or stave for vats/barrels for containing and/or refining beer, distillates of cereal, or sugar cane distillates.

7. A production line system for categorizing food-grade wooden part-components comprising:
    IR radiation emitting devices configured to irradiate the food-grade wooden part-components with an IR radiation beam;
    IR radiation sensitive means for receiving IR radiation reflected and/or transmitted by the irradiated food-grade wooden part-components and configured so as to generate a signal (S-IR) representing the radiation spectrum of the received IR radiation;

processing means configured to:
  determine, on the basis of said signal, the quantities (PE(i)) of odor active volatile compounds comprising lactones and/or eugenol present in the food-grade wooden part-components which, in use, condition the aroma/perfume of a wine, or wine-related product when the wine, or wine-related product, is put into contact with the food-grade wooden part-components themselves;
  compare at least said quantities (PE(i)) of odor active volatile compounds comprising lactones and/or eugenol with at least one predetermined reference magnitude (GE(i)) associated with a predetermined category of food-grade wood; and
  categorize said food-grade wooden part-components on the basis of the determined quantities (PE(i)) of odor active volatile compounds comprising lactones and/or eugenol;
  wherein the categorizing comprises determining whether the food-grade wooden part-components belong to said predetermined category of food-grade wood on the basis of said comparison; and
a wood processing station configured to receive the categorized food-grade wooden part-components and to sort each of the food-grade wooden part-components to one of at least two paths or stores based on the categorizing.

8. The system according to claim 7, wherein said processing means are further configured to:
  memorize at least a predetermined correlation function associated with quantities (PE(i)) of odor active volatile compounds to be determined; and
  perform an analysis algorithm to elaborate said spectrum of radiations reflected and/or transmitted by the irradiated food-grade wooden part-components by means of said predetermined correlation function in order to determine the quantities (PE(i)) of odor active volatile compounds.

9. The system according to claim 8, wherein said correlation function is determined by means of multivariate PCA (Principal Component Analysis) or PLS (Partial Least Squares) statistic processing methods/tests based on a series of samples data associated with the quantities (PE(i)) of odor active volatile compounds present in pre-established wood, and to the corresponding bands/wavelengths.

10. The system according to claim 7, wherein said food-grade wooden part-components comprise at least one plank/stave for vats/barrels for containing wine.

11. The system according to claim 7 wherein said food-grade wooden part-components comprise at least one plank or stave for vats/barrels for containing and/or refining beer, distillates of cereal, or sugar cane distillates.

12. The system according to claim 7 wherein said food-grade wooden part-components comprise wine refinement chips.

13. A machine for categorizing food-grade wooden staves comprising:
  IR radiation emitting devices configured for irradiating the food-grade wooden staves with IR radiation;
  IR radiation sensitive means for receiving IR radiation reflected by the irradiated food-grade wooden staves to generate a signal (S-IR) representing the radiation spectrum of the received IR radiation; and
  processing means configured to:
    determine, on the basis of said signal, the quantities (PE(i)) of odor active volatile compounds comprising lactones and/or eugenol present in the food-grade wooden staves which, in use, condition the aroma/perfume of a wine, or wine-related product when the wine, or wine-related product, is put into contact with the food-grade wooden staves themselves;
    compare at least said quantities (PE(i)) of odor active volatile compounds comprising lactones and/or eugenol with at least one predetermined reference magnitude (GE(i)) associated with a predetermined category of food-grade wood; and
    categorize said food-grade wooden staves on the basis of determined quantities (PE(i)) of the odor active volatile compounds comprising lactones and/or eugenol;
    wherein categorizing comprises determining whether the food-grade wooden staves belong to said predetermined category of food-grade wood on the basis of said comparison; and
  a wood processing station configured to receive the categorized food-grade wooden part-components and to sort each of the food-grade wooden part-components to one of at least two paths or stores based on the categorizing.

14. The machine according to claim 13 wherein said processing means are configured to:
  memorize at least a predetermined correlation function associated with quantities (PE(i)) of odor active volatile compounds to be determined;
  perform an analysis algorithm to elaborate said spectrum of radiations reflected and/or transmitted by the irradiated food-grade wooden staves, by means of said predetermined correlation function, in order to determine the quantities (PE(i)) of odor active volatile compounds.

* * * * *